US00PP17710P3

(12) United States Plant Patent
Abrahamson et al.

(10) Patent No.: US PP17,710 P3
(45) Date of Patent: May 8, 2007

(54) FAST-GROWING WILLOW SHRUB NAMED 'FISH CREEK'

(50) Latin Name: *Salix purpurea*
Varietal Denomination: Fish Creek

(75) Inventors: Lawrence P. Abrahamson, Marcellus, NY (US); Richard F. Kopp, Marietta, NY (US); Lawrence B. Smart, Geneva, NY (US); Timothy A. Volk, Syracuse, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 11/244,988

(22) Filed: Oct. 6, 2005

(65) Prior Publication Data

US 2007/0083964 P1 Apr. 12, 2007

(51) Int. Cl.
*A01H 5/00* (2006.01)

(52) U.S. Cl. ..... Plt./216

(58) Field of Classification Search ..... Plt./216
See application file for complete search history.

*Primary Examiner*—Kent Bell
(74) *Attorney, Agent, or Firm*—Wall Marjama & Bilinski LLP

(57) ABSTRACT

A distinct male cultivar of *Salix purpurea* named 'Fish Creek', characterized by rapid stem growth producing greater than 30% more woody biomass than either of its parents ('94001' and '94006') and 20% more biomass than a current production cultivar ('SV1'). 'Fish Creek' can be planted from dormant stem cuttings, produces multiple stems after coppice, and the stem biomass can be harvested when the plant is dormant. In the spring following harvest, the plant will re-sprout very vigorously, producing new stems that can be harvested after two to four years of growth. This harvest cycle can be repeated several times. The stem biomass can be chipped and burned as a source of renewable energy, generating heat and/or electricity. 'Fish Creek' displays a low incidence of rust disease or damage by beetles or sawflies.

11 Drawing Sheets

STATEMENT AS TO RIGHTS TO INVENTIONS MADE UNDER FEDERALLY-SPONSORED RESEARCH AND DEVELOPMENT

The invention described herein was reduced to practice during the funding period of Contract 4000003235 (SUNY Research Foundation Award 011275) awarded by Oak Ridge National Laboratory, managed by UT-Batelle for the United States Department of Energy under contract DE-AC05-00OR22725, and of agreement number 6267 (SUNY Research Foundation Award 011536) awarded by the New York State Energy Research and Development Authority.

CROSS-REFERENCE TO RELATED APPLICATIONS

This application is related to the following plant patent applications, all of which are subject to assignment to the Research Foundation of the State University of New York, and each of which is being filed on even date herewith: "Fast-Growing Shrub Willow" Named 'Canastota', application Ser. No. 11/244,986, "Fast-Growing Shrub Willow" Named 'Millbrook', application Ser. No. 11/244,636, "Fast-Growing Shrub Willow" Named 'Oneida', application Ser. No. 11/244,975, "Fast-Growing Shrub Willow" Named 'Otisco', application Ser. No. 11/244,987, "Fast-Growing Shrub Willow" Named 'Owasco', application Ser. No. 11/244,842; and "Fast-Growing Shrub Willow" Named 'Tully Champion', application Ser. No. 11/244,635. The variety of fast-growing shrub willow named 'Fish Creek' was produced in the willow breeding program at the State University of New York College of Environmental Science and Forestry, as were other varieties, including: 'Canastota', 'Millbrook', 'Oneida', 'Otisco', 'Owasco', and 'Tully Champion'.

BACKGROUND OF THE INVENTION

1. Field of the Invention

The invention is a new and distinct cultivar of *Salix purpurea* known by the varietal name 'Fish Creek'. The new variety was produced through controlled willow breeding conducted by the inventors at the State University of New York College of Environmental Science and Forestry in Syracuse, N.Y. The objective of the breeding program is to produce new willow cultivars that generate high biomass yields on a variety of sites, are resistant to diseases and pests, and possess agronomic traits suitable for mechanical planting, harvesting, and post-harvest processing to provide a sustainable, renewable source of energy. Once a field planting of shrub willows is established, the woody stems can be harvested every three years, and new shoots will re-sprout the following season. Repeated harvesting every two to four years can be sustained for at least 15 years.

2. Description of Relevant Prior Art Including Information Disclosed Under 37 CRF 1.97–1.99

This new variety of *Salix purpurea* was the seedling progeny of the controlled pollination of a female clone (ID# 94006) of *Salix purpurea* by a male clone of *Salix purpurea* (ID# 94001) performed in February 1998 in Syracuse, N.Y. The plant has been propagated repeatedly by stem cuttings and has been found to retain its distinctive characteristics through successive propagations and field trials. More specifically, the plant has been asexually reproduced by collecting dormant stems during the winter months from a plant growing in Syracuse, N.Y.; cutting them into either 5" or 10" pieces (cuttings); then planting those cuttings in the field in Tully, N.Y. in the spring or in potting mix in the greenhouse, then transplanting the rooted cuttings to the field in Tully, N.Y.

Both parents (94006 and 94001) were originally identified in 1994 growing on the shores of creeks in Oneida County, N.Y. and were vegetatively propagated from stem cuttings. The new variety is distinguished from the female parent in that it is male. The growth of the parent plants was characterized in nursery plantings. Both parents displayed rapid stem growth and low incidence of rust disease, so were chosen to serve as parents in a cross. The seedlings produced by this cross (identification #9882) were first established in a greenhouse, and then were transplanted to a field. This particular individual (identification #9882-34) shown in the Figures was selected from the family due to its exceptional stem height growth.

The new cultivar has been grown in Syracuse, N.Y. and Tully, N.Y., which have a normal yearly average daily temperature of 47° F., normal daily maximum temperature in July of 82° F., normally daily minimum temperature in January of 14° F., and average precipitation of 40 inches. The new cultivar grows from a rooted cutting to a fully mature plant ready for harvest in approximately three years.

SUMMARY OF THE INVENTION

The *Salix purpurea* cultivar 'Fish Creek' has not been observed under all possible environmental conditions. The phenotype may vary somewhat with variations in environments such as temperature, light intensity and length of illumination, without, however, any variation in genotype. The new and distinct cultivar presents the following traits that have been repeatedly observed and are determined to be the unique characteristics of 'Fish Creek'. These characteristics in combination distinguish 'Fish Creek' as a new and distinct cultivar:

1. Rapid growth rate, producing greater than 30% more woody biomass than its parents when grown in the same field for the same length of time (three growing seasons after coppice) in Tully, N.Y.
2. Low incidence of rust disease or damage by beetle or sawfly as scored by visual inspection.

BRIEF DESCRIPTION OF THE DRAWING

The accompanying color photographs show the features of the claimed cultivar in a manner as true as is reasonably possible. The illustrations include:

FIG. 1.1 illustrates one-year-old portion of stem collected while dormant;

FIG. 1.2 illustrates one-year-old portion of stem collected while dormant;

FIG. 1.3 illustrates a vegetative bud in dormancy;

FIG. 1.4 illustrates a floral bud in dormancy;

FIG. 1.5 illustrates new shoot growth from a stem cutting rooted in sand:potting mix in a greenhouse;

FIG. 1.6 illustrates upper leaf surface;

FIG. 1.7 illustrates lower leaf surface;

FIG. 1.8 illustrates catkin with anthers;

FIG. 1.9 illustrates stamen and densely pubescent bud scale;

FIG. 2.1 illustrates stem area one year after coppice for the claimed cultivar as compared to other shrub willows;

FIG. 2.2 illustrates dry stem biomass yield three years after coppice for the claimed cultivar as compared to other shrub willows.

DETAILED DESCRIPTION OF THE NEW PLANT

The following detailed description sets forth characteristics of the new plant. The following observations and measurements describe plants grown by asexual reproduction in Syracuse, N.Y. or Tully, N.Y. under conditions as described hereinabove. Color references are made using The Royal Horticultural Society Colour Chart (hereinafter The R.H.S. Colour Chart) of The Royal Horticultural Society of London, England, except where general terms of ordinary dictionary significance are used.

BOTANICAL DESCRIPTION OF THE PLANT

The following detailed botanical description of the 'Fish Creek' variety is based on observations from 10 inch cuttings grown in a greenhouse in Syracuse, N.Y. Cuttings were grown in 7 inch tubes in a (1:1) ProMix®/sand (v/v) substrate under natural light from December 2004 to March 2005. Plants were irrigated with automatic misting for 6 minutes at 2 hours intervals five times each day.

Latin name: *Salix purpurea.*
Varietal denomination: 'Fish Creek'.
Parentage:
*Female or seed parent.*—*S. purpurea* '94006'.
*Male or pollen parent.*—*S. purpurea* '94001'.
Propagation:
*Type.*—Stem cuttings.
*Time to rooting.*—Approximately 10 days in water at 21° C.
Precocity: Precocious — Catkins mature several days before leaves break bud.
Plant description: The color of one-year-old stems observed when dormant is typically brown (RHS 177A) on the newest portions, while older portions are smooth, glaucous, and green (RHS 146C). Dormant vegetative buds produced during the previous growing season are yellow to orange (RHS 162A, RHS 171A), 6 mm in length, ovoid, and acute. Lenticels are small, sparse, reddish, and 1 mm in diameter. The leaves are simple and opposite to subopposite (occasionally alternate) with pinnate venation. Typical petioles on mature leaves grown under field conditions in early October are 2 mm in length, yellow-green (#145A), and 1.0–2.0 mm in diameter. The petiole on the leaf in FIGS. 1.6–1.7 from a greenhouse-grown plant is green (#143D) and 1.0–1.5 mm wide. There are no stipules. Immature leaves are glabrous. Mature leaves are oblong, obtuse apex, obtuse base, typically 6.1–6.9 cm in length, 1.6–2.1 cm in width, with slightly serrate to subentire margins, curved, adaxial (upper) surface dark green (RHS 143A) with glaucous flakes, abaxial (lower) surface light pale green (RHS 144B), and stem light pale green (RHS 145B) at 7½ weeks of growth. The typical diameter of two-year old stems at a height of 1 m is 1.3 cm. The bark color of field-grown stems determined in early October after two growing seasons is yellow-green (#147B). The surface is fairly smooth with shallow thin longitudinal furrows and raised reddish lenticels. The average plant height of a mature plant after three seasons of growth is 5–6 m with a typical spread at the crown of 1.0–1.5 m when grown in the typical planting spacing of 0.6 m×0.7 m.

Flowering description: Dormant floral buds are elongated, acute, 11 mm in length, appressed, diameter rounded, and brown (RHS 165A) to golden-brown (RHS 165B). Peduncle of catkin is short and bears four leaf-like bracts, approximately 4 mm in length. Catkins are erect, 2.2–2.4 cm in length, narrowly cylindrical, and densely flowered. Flowers have one stamen and one nectary, a densely pubescent floral bract, thick filament, orange immature anthers, and yellow-brown mature anthers.

Field growth characteristics: Determined through surveys of plants growing in the field in Tully, N.Y.

Disease and insect resistance: Leaves display low incidence of beetle damage and stems display low incidence of sawfly damage — scored as a 1 (on a scale of 1 to 3, with 1 being the least amount of damage and 3 the greatest) in a field surveys conducted in August and September 2001. Leaves are largely resistant to rust as scored by visual inspection at the end of each growing season.

Temperature tolerance: Stems typically do not suffer frost damage at temperatures as low as 10° F. and may suffer only minor tip dieback at lower temperatures.

Seed production: None — does not produce female flowers.

Stem growth and biomass yield: Mean total area of stems produced through one growing season after coppice in each of three 20 plant plots ('Fish Creek', 142 $cm^2$) measured in a yield trial growing in Tully, N.Y. in April 2003 was greater than the mean stem area of either parent ('94001', 90 $cm^2$; '94006', 114 $cm^2$) and was greater than a current production cultivar ('SV1', 104 $cm^2$) growing in the same trial (FIG. 2.1).

Total dry stem biomass yield ('Fish Creek' 53,500 kg per hectare) harvested after three growing seasons after coppice in February and March 2005 in the same trial described above was more than 30% greater than either parent ('94001' 39,900 kg per hectare; '94006' 39,100 kg per hectare) and 20% greater than the biomass produced by a current production cultivar ('SV1' 44,400 kg per hectare) (FIG. 2.2).

What is claimed is:

1. A new and distinct variety of a *Salix purpurea* plant, substantially as illustrated and described herein.

* * * * *

Fig. 1.1
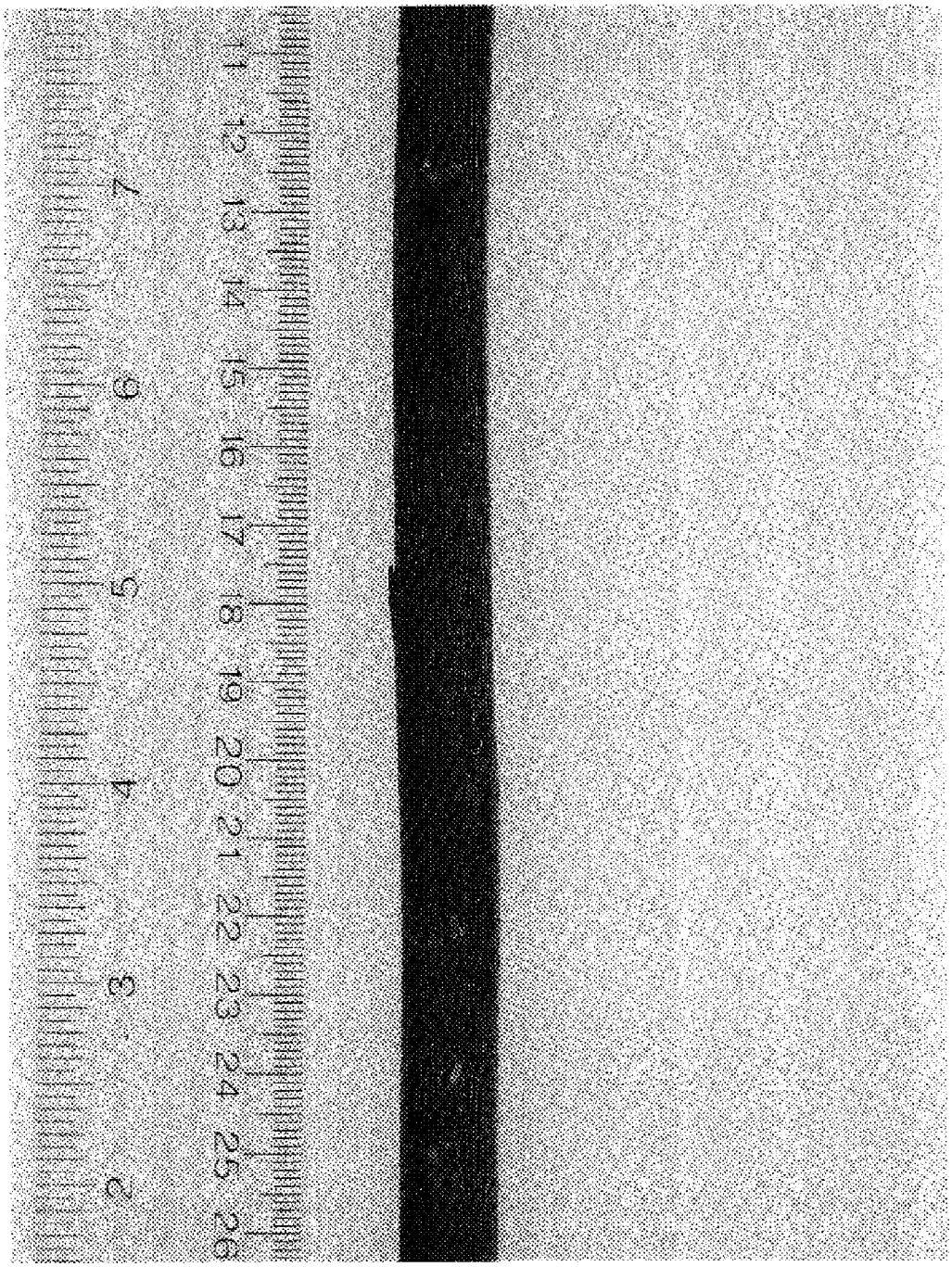

Fig. 1.2
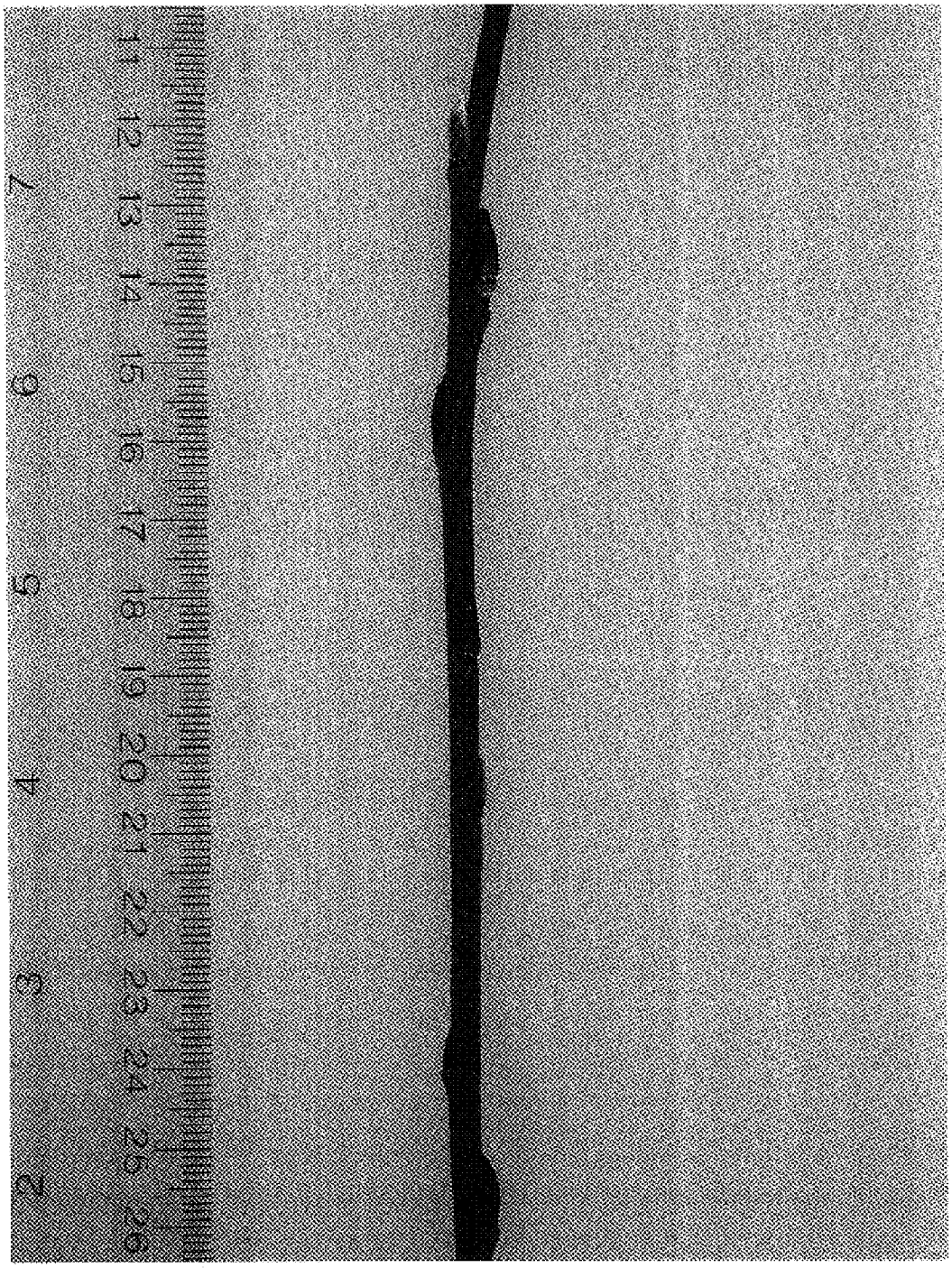

Fig. 1.3
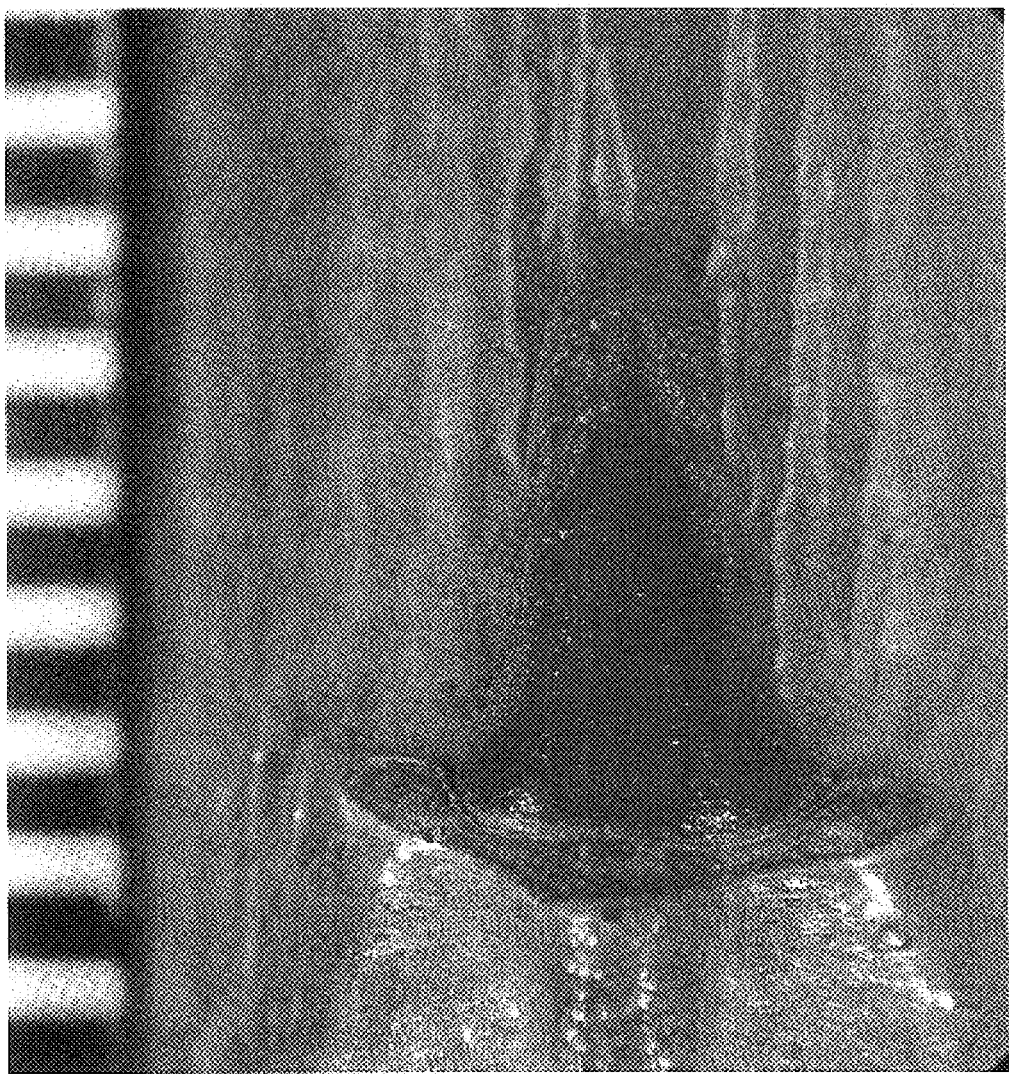

Fig. 1.4
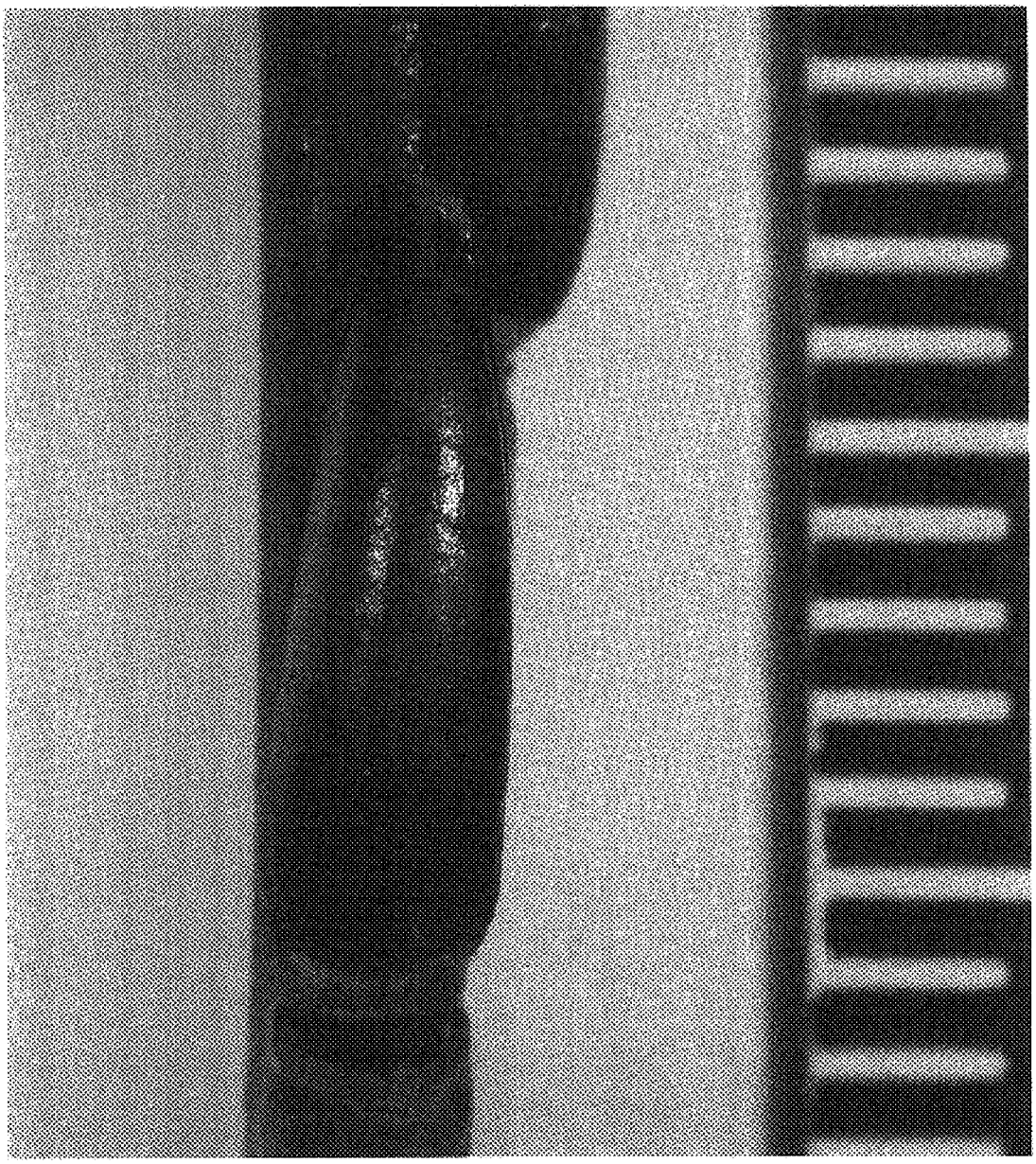

Fig. 1.5
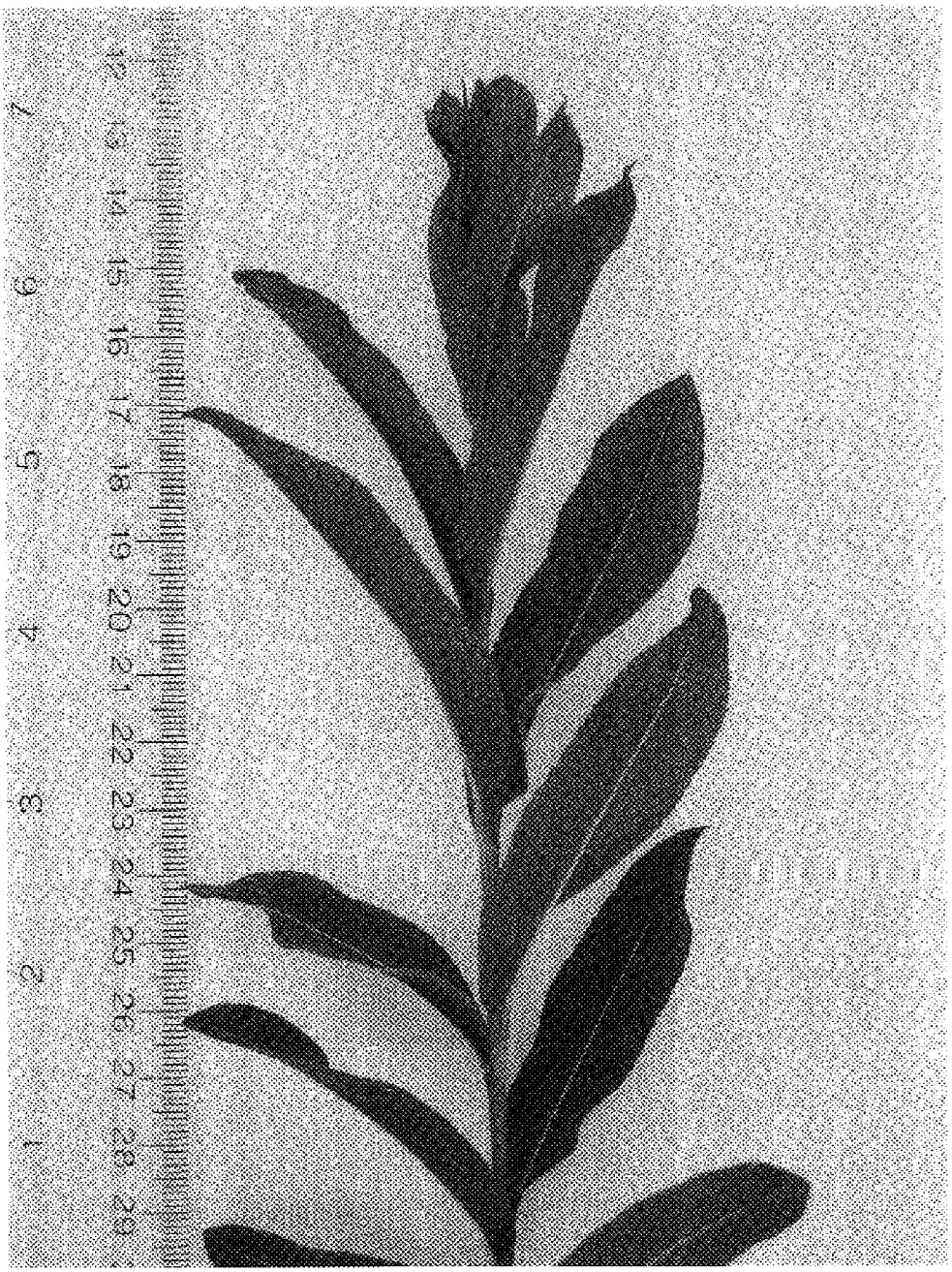

Fig. 1.6
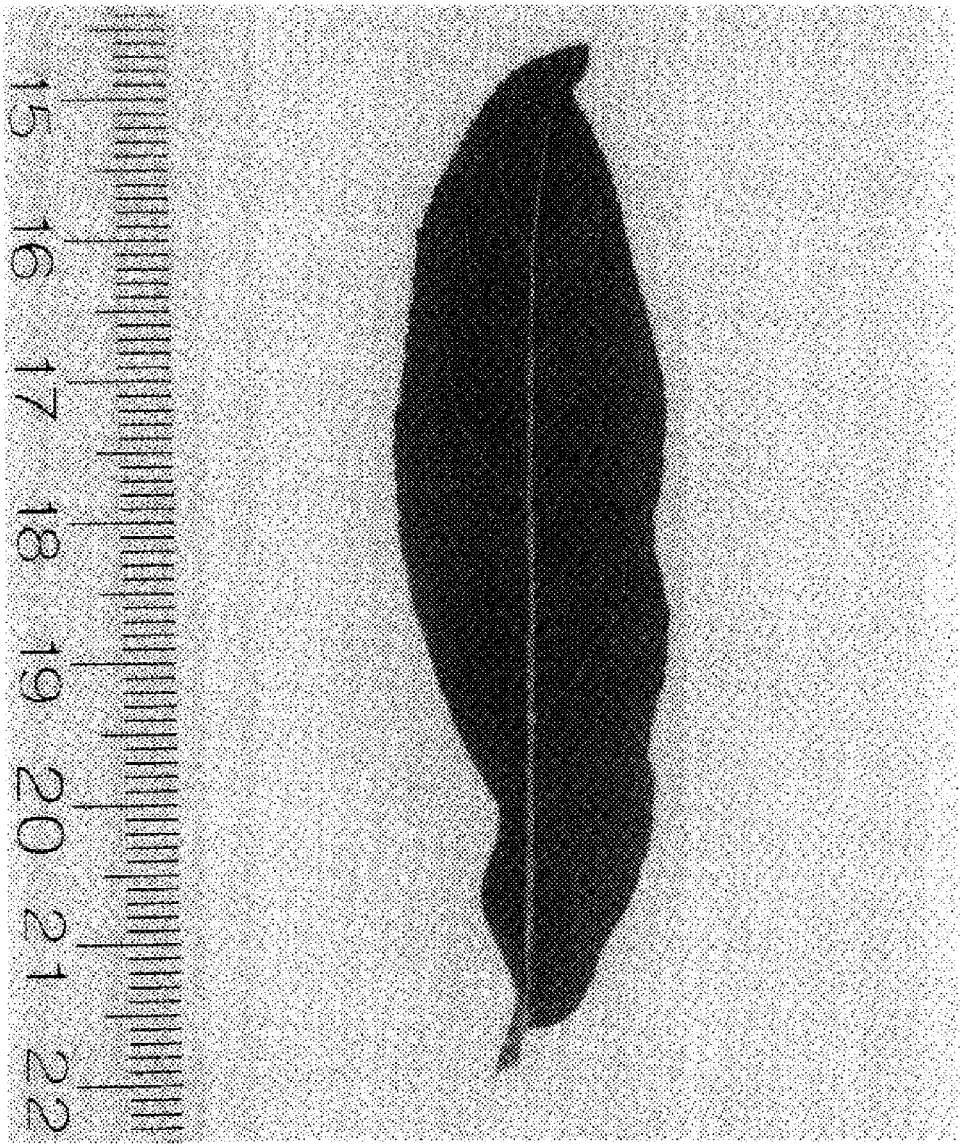

Fig. 1.7
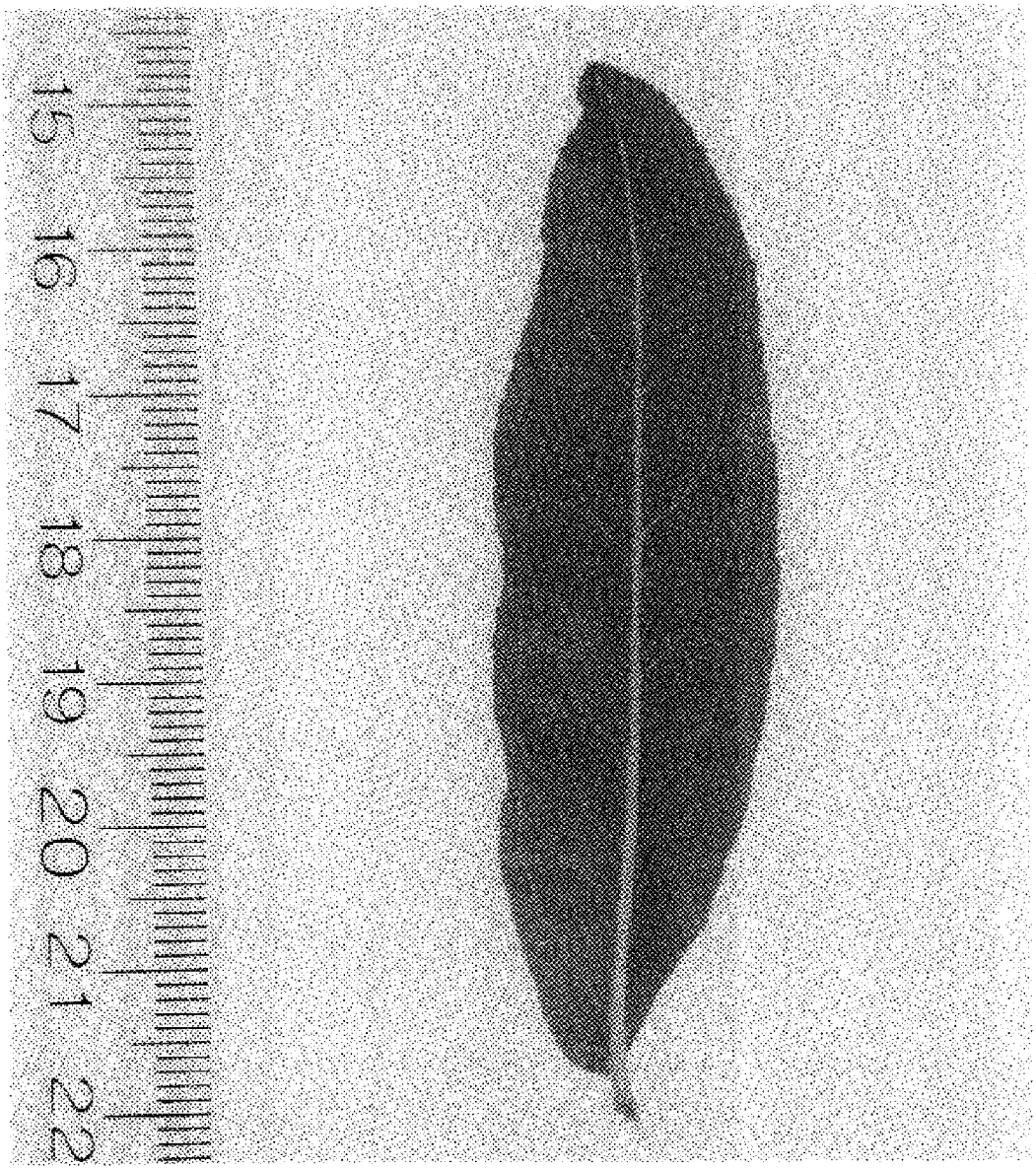

Fig. 1.8
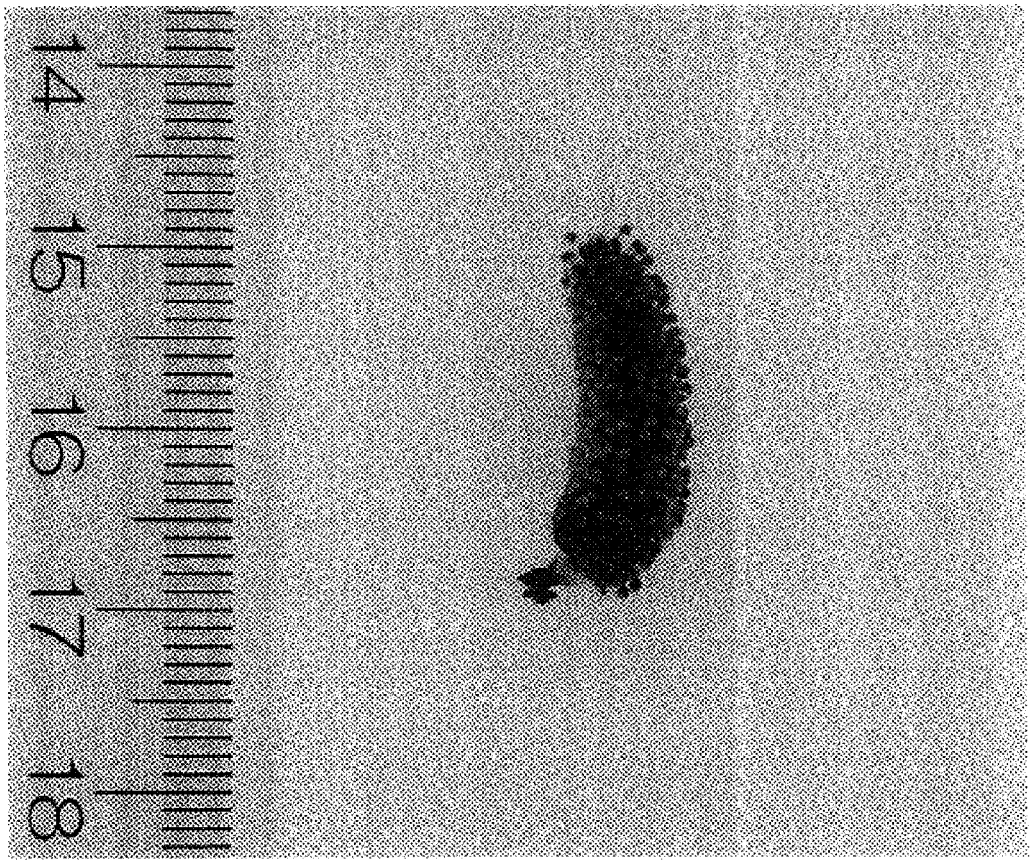

Fig. 1.9
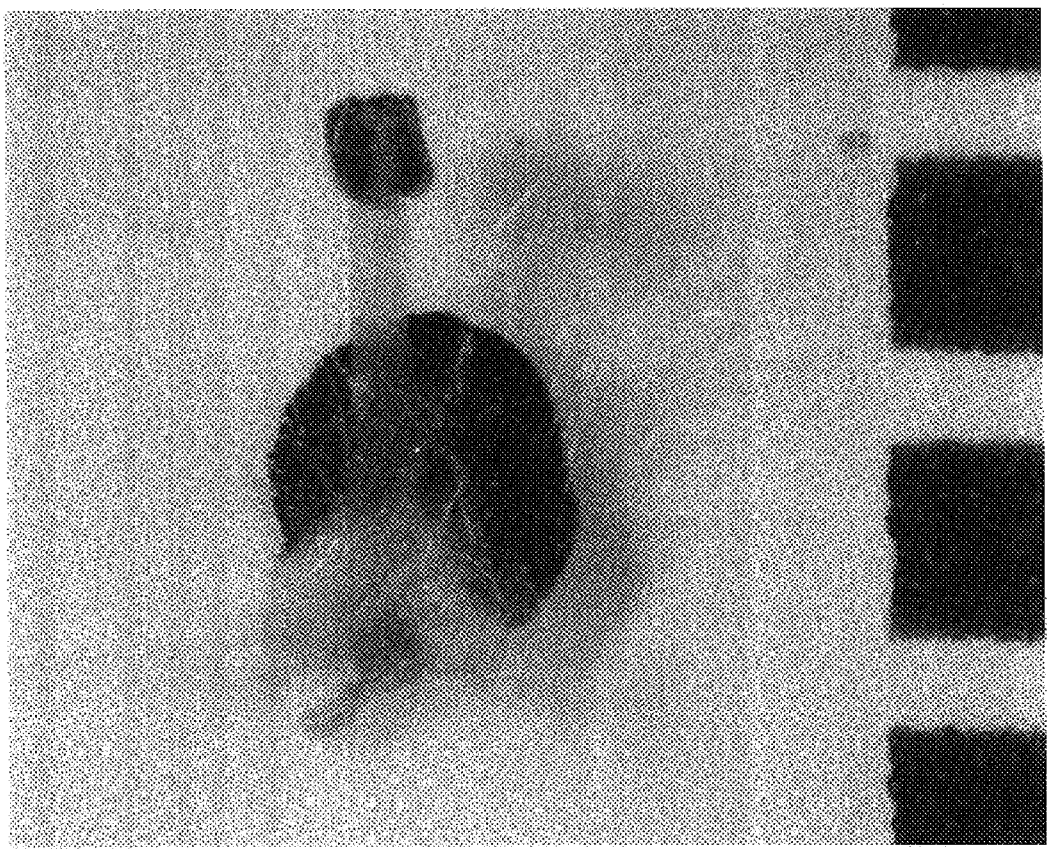

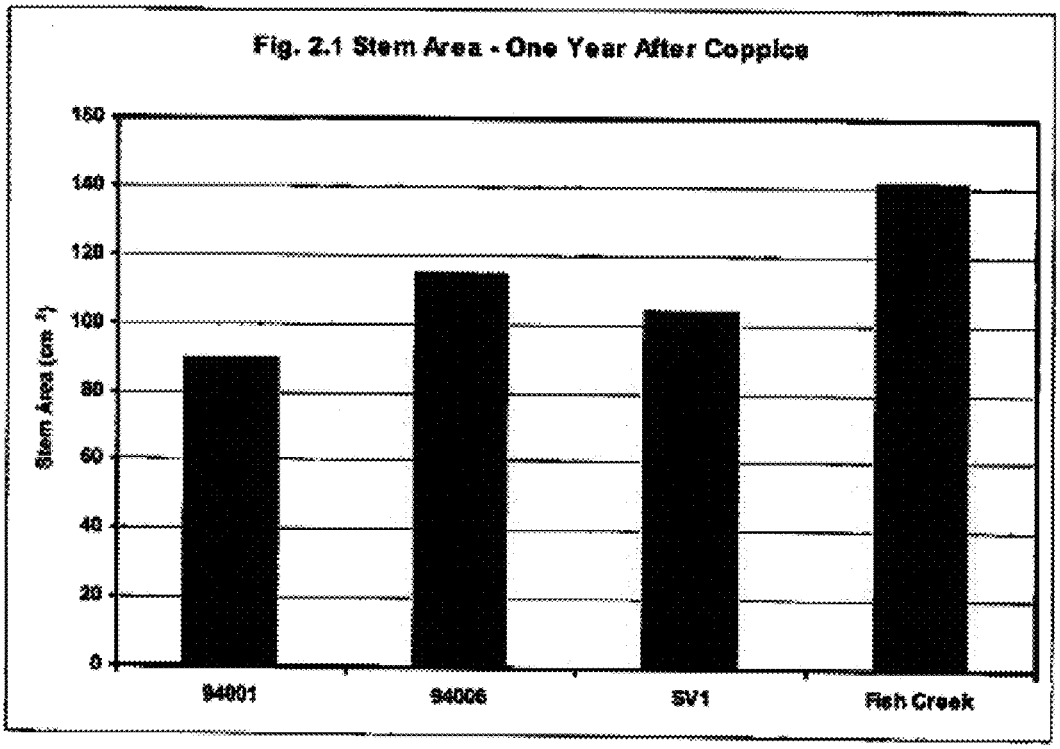
Fig. 2.1 Stem Area - One Year After Coppice
Stem Area (cm 2)
160
140
120
100
80
60
40
20
0
94001
94006
SV1
Fish Creek

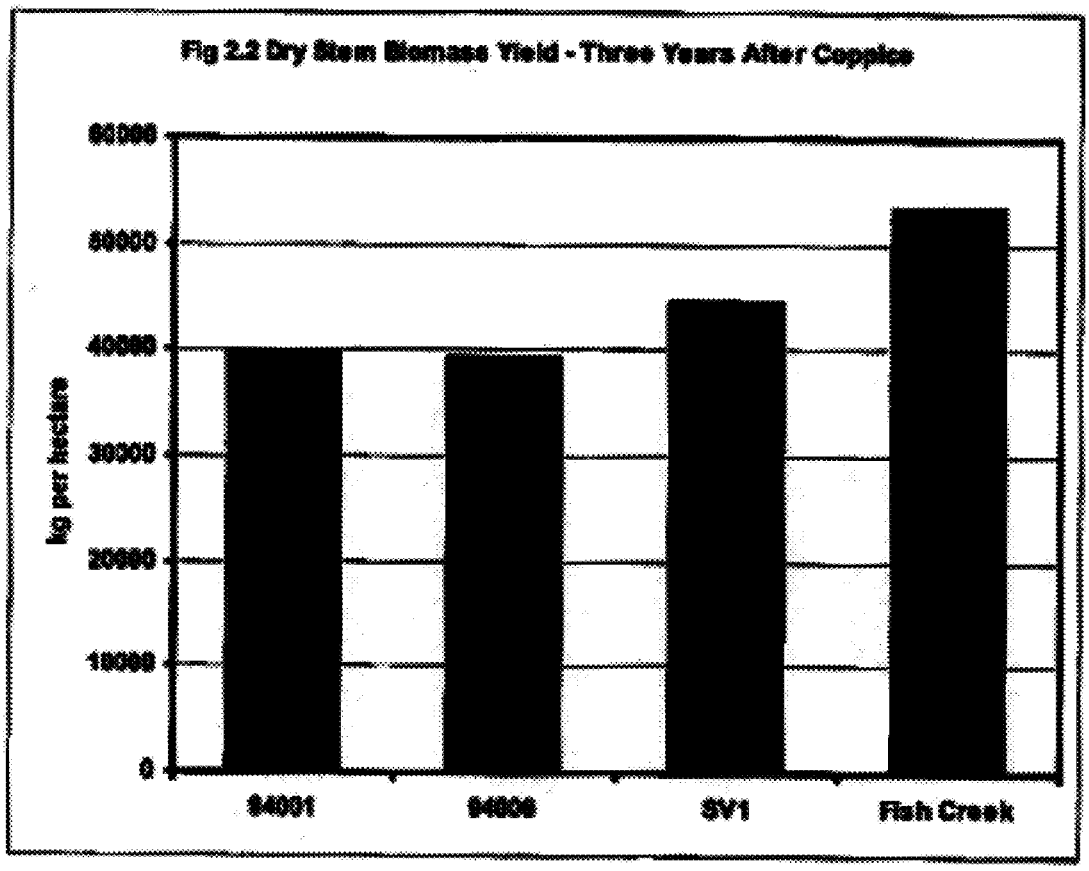
Fig 2.2 Dry Stem Biomass Yield - Three Years After Coppice
kg per hectare
60000
50000
40000
30000
20000
10000
0
94001
94006
SV1
Fish Creek